United States Patent
Mensch et al.

(10) Patent No.: US 12,121,323 B2
(45) Date of Patent: Oct. 22, 2024

(54) CORE TEMPERATURE DETECTION SYSTEM AND METHOD

(71) Applicant: Robert Bosch GmbH, Stuttgart (DE)

(72) Inventors: Beatrix Mensch, Illertissen (DE); Thomas Rocznik, Mountain View, CA (US); Christian Peters, Sunnyvale, CA (US); Seow Yuen Yee, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 646 days.

(21) Appl. No.: 16/957,252

(22) PCT Filed: Dec. 21, 2018

(86) PCT No.: PCT/US2018/067033
§ 371 (c)(1),
(2) Date: Jun. 23, 2020

(87) PCT Pub. No.: WO2019/133469
PCT Pub. Date: Jul. 4, 2019

(65) Prior Publication Data
US 2020/0397305 A1    Dec. 24, 2020

Related U.S. Application Data (60) Provisional application No. 62/626,537, filed on Feb. 5, 2018, provisional application No. 62/611,029, filed on Dec. 28, 2017.

(51) Int. Cl.
*A61B 5/01*     (2006.01)
*A61B 5/00*     (2006.01)

(52) U.S. Cl.
CPC .............. *A61B 5/01* (2013.01); *A61B 5/6831* (2013.01); *A61B 5/6832* (2013.01);
(Continued)

(58) Field of Classification Search
CPC ......... A61B 5/01; A61B 5/683; A61B 5/6832; A61B 2503/40; A61B 2560/0214;
(Continued)

(56) References Cited

U.S. PATENT DOCUMENTS 6,056,435 A    5/2000  Pompei
6,908,224 B2   6/2005  Schneider et al.
(Continued)

FOREIGN PATENT DOCUMENTS

CN    101112306 A    1/2008
WO    2017/204733 A1   11/2017

OTHER PUBLICATIONS

International Search Report corresponding to PCT Application No. PCT/US2018/067033, mailed Apr. 18, 2019 (4 pages).
(Continued)

*Primary Examiner* — Eric F Winakur
*Assistant Examiner* — Abid A Mustansir
(74) *Attorney, Agent, or Firm* — Maginot, Moore & Beck LLP (57) ABSTRACT

A method for calibrating a thermometer unit for measuring a core temperature of a system, includes determining a first heat transfer coefficient of the system, and calculating core temperature data corresponding to the core temperature of the system based on the first heat transfer coefficient. The method also includes identifying a change in the core temperature data that exceeds a predetermined threshold. The thermometer unit is calibrated by determining a second heat transfer in response to the identified change in the core temperature data. The core temperature data is calculated based on the second heat transfer coefficient.

15 Claims, 6 Drawing Sheets

(52) U.S. Cl.
CPC ... *A61B 2503/40* (2013.01); *A61B 2560/0214* (2013.01); *A61B 2560/0223* (2013.01); *A61B 2560/0252* (2013.01); *A61B 2562/0271* (2013.01)

(58) Field of Classification Search
CPC .... A61B 2560/0223; A61B 2560/0252; A61B 2562/0271; A61B 2560/0247; A61B 5/6802
See application file for complete search history.

(56) References Cited

U.S. PATENT DOCUMENTS

| | | |
|---|---|---|
| 2006/0222048 A1 | 10/2006 | Pompei |
| 2009/0154519 A1* | 6/2009 | Price .................. G01J 5/16 374/1 |
| 2013/0085708 A1 | 4/2013 | Sattler |
| 2013/0158376 A1 | 6/2013 | Hayter et al. |
| 2019/0285488 A1* | 9/2019 | Lundström ............ G01K 13/20 |

OTHER PUBLICATIONS

Marz, M. et al. "Thermal Modeling of Power-electronic Systems," Infineon Technologies AG. Munich, Feb. 2000.

* cited by examiner

CORE TEMPERATURE DETECTION SYSTEM AND METHOD

This application is a 35 U.S.C. § 371 National Stage Application of PCT/US2018/067033, filed on Dec. 21, 2018, which claims the benefit of priority of U.S. provisional application Ser. No. 62/611,029, filed on Dec. 28, 2017 and U.S. provisional application Ser. No. 62/626,537, filed on Feb. 5, 2018, the disclosures of which are herein incorporated by reference in their entireties.

FIELD

This disclosure relates to the field of temperature sensing and, in particular, to sensing a core temperature of a human, an animal, or a machine.

BACKGROUND

Core temperature, also called core body temperature, is an important metric in the health condition of a person. Core body temperature is the temperature of the internal environment of the body. A normal core body temperature is about 37° C. A core body temperature above about 41° C. or below about 32° C. should prompt a person to seek immediate attention from a medical professional.

Medical professionals use thermometers to measure the core body temperature of a patient during medical emergencies as well as during routine examinations. Direct measurement of core body temperature is typically an invasive procedure requiring the placement of a probe within a body cavity. As an alternative, core body temperature is estimated or calculated by measuring the temperature of various other sites, such as an oral temperature, an underarm temperature, and a temperature on the skin of the forehead.

It is desired that the estimated core body temperature is an accurate representation of the actual core body temperature. Accordingly, further advancements in the area of core body temperature estimation, detection, and calculation are desirable.

SUMMARY

According to an exemplary embodiment of the disclosure, a method for determining a core temperature of a system with a thermometer unit includes calculating a first core temperature of the system based on a heat transfer coefficient at a first time with a controller of the thermometer unit, storing the calculated first core temperature as first core temperature data in a memory unit of the thermometer unit. The method also includes calculating a second core temperature of the system based on the heat transfer coefficient at a second time after the first time with the controller, and storing the calculated second core temperature as second core temperature data in the memory unit. Additionally, the method includes determining temperature difference data as a difference between the calculated first and second core temperature data with the controller. When the temperature difference data is greater than a predetermined temperature difference threshold, the method includes (i) recalculating the heat transfer coefficient with the controller, (ii) deleting the second core temperature data from the memory, and (iii) calculating a third core temperature of the system based on the recalculated heat transfer coefficient, and storing the recalculated core temperature as third core temperature data in the memory.

According to another exemplary embodiment of the disclosure, a thermometer unit for determining a core temperature of a system includes a temperature sensor, a heat flux sensor, a memory, and a controller. The temperature sensor is configured to sense a surface temperature of the system and to generate temperature data corresponding to the sensed surface temperature. The heat flux sensor is configured to sense a heat flux of the system and to generate heat flux data corresponding to the sensed heat flux. The memory is configured to store the temperature data and the heat flux data. The controller is operably connected to the temperature sensor, the heat flux sensor, and the memory and is configured to determine core temperature data corresponding to a core temperature of the system. The controller is configured to calibrate the thermometer unit in response to an environmental influence by calculating first core temperature data based on a first sensed surface temperature, a first sensed heat flux, and a heat transfer coefficient at a first time, calculating second core temperature data based on a second sensed surface temperature, a second sensed heat flux, and the heat transfer coefficient at a second time, and calibrating thermometer unit if a difference between the first core temperature data and the second core temperature data exceeds a predetermined threshold value by calculating another heat transfer coefficient.

According to yet another exemplary embodiment of the disclosure, a method for calibrating a thermometer unit for measuring a core temperature of a system, includes determining a first heat transfer coefficient of the system, and calculating core temperature data corresponding to the core temperature of the system based on the first heat transfer coefficient. The method also includes identifying a change in the core temperature data that exceeds a predetermined threshold, calibrating the thermometer unit by determining a second heat transfer in response to the identified change in the core temperature data, and calculating the core temperature data based on the second heat transfer coefficient.

BRIEF DESCRIPTION OF THE FIGURES

The above-described features and advantages, as well as others, should become more readily apparent to those of ordinary skill in the art by reference to the following detailed description and the accompanying figures in which.

DETAILED DESCRIPTION

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

For the purposes of the disclosure, the phrase "A and/or B" means (A), (B), or (A and B). For the purposes of the disclosure, the phrase "A, B, and/or C" means (A), (B), (C), (A and B), (A and C), (B and C), or (A, B and C).

The terms "comprising," "including," "having," and the like, as used with respect to embodiments of the disclosure, are synonymous.

Figure 1:
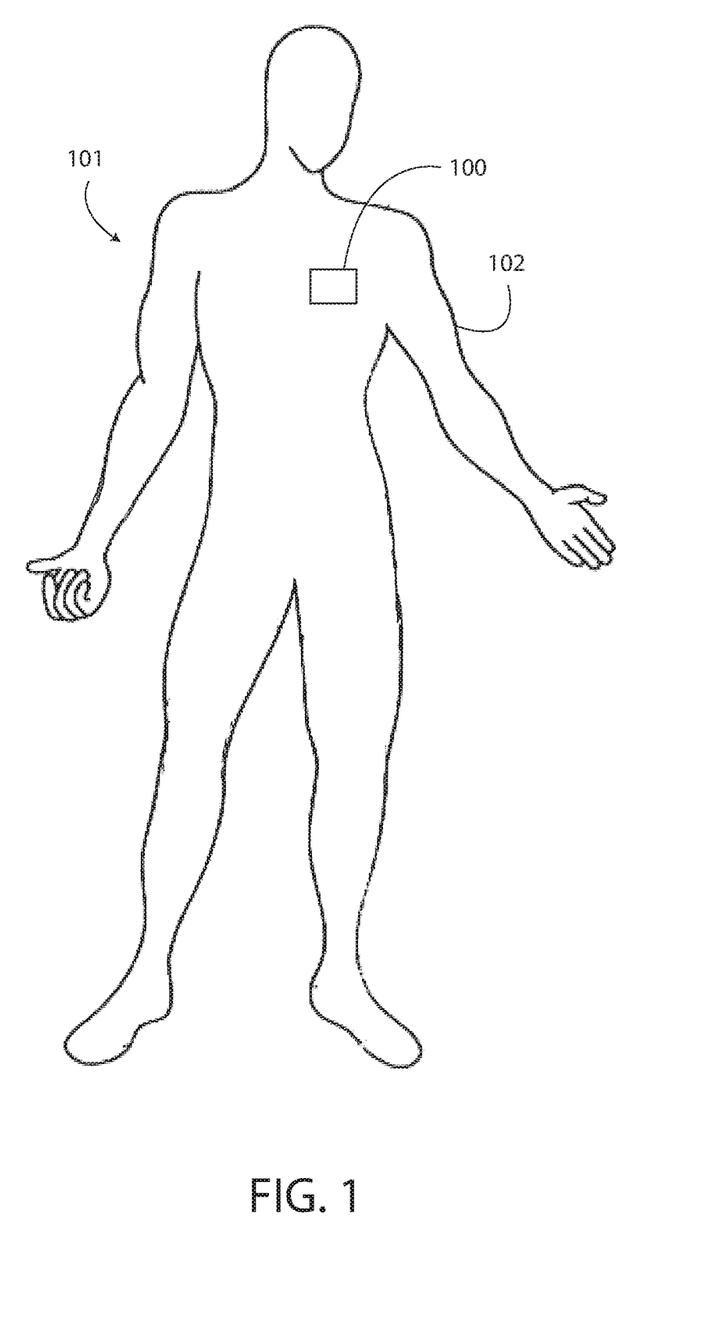
FIG. 1 is a diagram of a patient and a thermometer unit, as disclosed herein, applied to the skin of the patient.

As shown in FIG. 1, a thermometer unit 100 is mounted on a system 101 shown as a human body or a human patient. The thermometer unit 100 is configured to determine the patient's core temperature (also referred to herein as a "core body temperature"). Moreover, the thermometer unit 100 is configured to calibrate itself in response to an environmental influence 180 (FIGS. 5 and 6) by adjusting a heat transfer coefficient ("hs") used to calculate the core temperature. Thus, for example, the thermometer unit 100 can accurately determine the patient's core temperature when the patient moves from a cold environment to a warm environment. The patient, therefore, is not restricted to a particular location while wearing the thermometer unit 100. The thermometer unit 100 is non-invasive and is mounted on the skin 102 of the patient or the surface of the system 101. The thermometer unit 100 monitors the patient's core body temperature quickly and accurately, and generates corresponding electronic core temperature data. Moreover, the thermometer unit 100 accurately estimates and/or calculates the core temperature for all types of patients independent of gender, weight, height, and body mass index. Each element of the thermometer unit 100 and a method 300 (FIG. 3) of operating the thermometer unit 100 are described herein.

Figure 2:
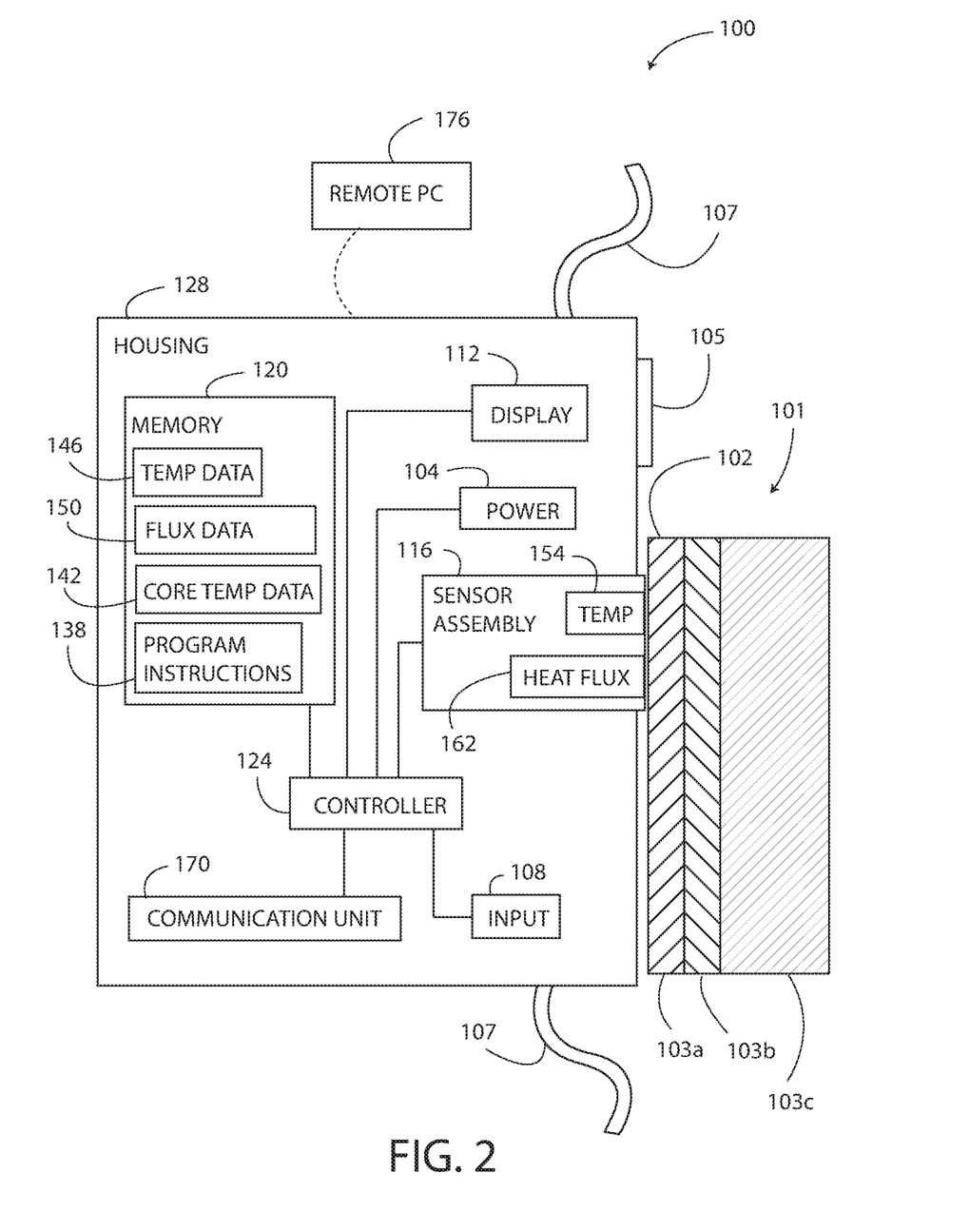
FIG. 2 is a block diagram of the thermometer unit of FIG. 1 and a cross section of a portion of the skin of the patient.

With reference to FIG. 2, the thermometer unit 100 includes an adhesive portion 105 and a strap 107. The adhesive portion 105 is configured to non-invasively mount the thermometer unit 100 onto the surface of the system 101. In the illustrated example, the adhesive portion 105 is a skin-safe adhesive that bonds to the skin 102 of the patient, and that positions the thermometer unit 100 at a suitable location for determining the core temperature.

The strap 107 is similarly configured to non-invasively mount the thermometer unit 100 on the surface of the system 101 at a suitable location for determining the core temperature. The strap 107 is useable as a supplemental restraint in addition to the adhesive portion 105, or a standalone means of mounting the thermometer unit 100 to the patient without the adhesive portion 105. In another embodiment, the thermometer unit 100 does not include the adhesive portion 105 or the strap 107, and the thermometer unit 100 is held against the system 101 by a user in order to determine the core temperature.

The thermometer unit 100 further includes a power supply 104, an input unit 108, a display 112, a sensor assembly 116, a memory unit 120, and a communication unit 170 operably connected to a controller 124. The power supply 104, the input unit 108, the display 112, the sensor assembly 116, the memory unit 120, the communication unit 170, and the controller 124 are each at least partially located within a housing 128. In one embodiment, the housing 128 is configured to be gripped by a user during operation of the thermometer unit 100.

The power supply 104, in one embodiment, includes a battery. For example, the power supply 104 is a rechargeable lithium polymer battery. Accordingly, the thermometer unit 100 is cordless in use and does not require a wired connection to a mains power supply. In other embodiments, the power supply 104 is provided as any other power source, such as an energy harvester with a power management circuit.

The memory 120 of the thermometer unit 100 is an electronic data storage unit, which is also referred to herein as a non-transient computer readable medium. The memory 120 is configured to store program instruction data 138, core temperature data 142, temperature data 146, heat flux data 150, and other electronic data associated with operation of the thermometer unit 100.

The input unit 108 is configured to receive input data via manipulation by a user. The input unit 108 may be configured as a touchscreen applied over the display 112 that is configured to enable a user to input data via the touch of a finger and/or a stylus. In another embodiment, the input unit 108 comprises any device configured to receive user inputs, as may be utilized by those of ordinary skill in the art, including e.g., one or more buttons, switches, keys, and/or the like.

The display 112 is configured to display a visual representation of at least the core temperature data 142. The display 112 may comprise a liquid crystal display (LCD) panel configured to display static and dynamic text, images, and other visually comprehensible data. The display 112, in another embodiment, is any display unit as desired by those of ordinary skill in the art.

The controller 124 of the thermometer unit 100 is configured to execute the program instruction data 138 for controlling the sensor assembly 116 and determining/calculating the core temperature of a patient or a machine, which is stored as the core temperature data 142 in the memory 120. The controller 124 is provided as a microprocessor, a processor, or any other type of electronic control chip.

With continued reference to FIG. 2, the sensor assembly 116 includes a temperature sensor 154 and a heat flux sensor 162. The temperature sensor 154 is configured to measure a surface temperature of the system 101. The surface temperature does not typically correspond to the core temperature of system 101. For example, when the system 101 is a human patient, the surface temperature is a temperature of the patient's skin 102 and is less than the core temperature. The skin 102 includes an epidermis layer 103a, a dermis layer 103b, and a hypodermis layer 103c. The temperature sensor 154 is configured for placement directly against a surface of the patient's epidermis 103a, which is referred herein simply as the patient's skin 102. The temperature sensor 154 generates an electrical temperature output signal based on the sensed temperature. The electrical temperature output signal is received by the controller 124 and includes the temperature data 146, which is also referred to herein as skin temperature data 146.

The heat flux sensor 162 is configured to measure heat flux at the surface of a system 101, such as the patient's skin 102. In one embodiment, the heat flux sensor 162 is configured for placement directly against the patient's skin 102. The "heat flux" corresponds to a measured heat rate divided by a surface area of the heat flux sensor 162. Heat rate corresponds to the rate at which the system 101 radiates or loses heat. The heat flux sensor 162 generates an electrical output signal (typically a voltage) based on the sensed heat flux. The electrical output signal generated by the heat flux sensor 162 is received by the controller 124 and includes the heat flux data 150.

The communication unit 170 is a wireless or wired data transceiver unit that is configured to transmit data to an end device 176 and to receive data from the end device 176. For example, the communication unit 170 is configured to transmit at least some of the electronic data stored in the memory 120 (i.e. computed results, such as the core temperature data 142) to the end device 176, which is provided as a smartphone, PC, laptop, or the like. In some embodiments, instead of the controller 124 generating the core temperature data 142, the end device 176 generates the core temperature data 142 and transmits the core temperature data 142 to the thermometer unit 100 to be stored in the memory 120 via the Internet. In such an embodiment, the communication unit 170 receives the core temperature data 142 from the end device 176. In a further embodiment, the core temperature data 142 is generated in the cloud, transmitted to the thermometer unit 100 via the Internet, and received by the communication unit 170 to be stored in the memory 120.

Figure 3:
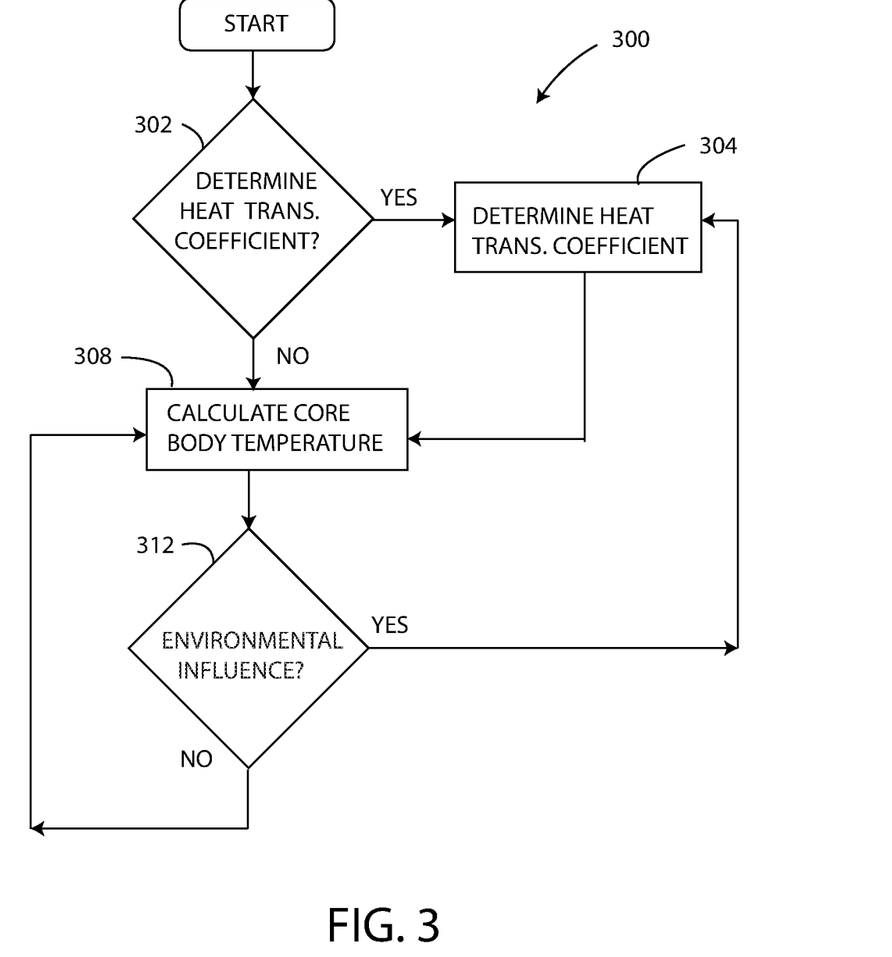
FIG. 3 is a flowchart illustrating an exemplary method for operating the thermometer unit of FIG. 1.

In operation, the thermometer unit 100 determines a patient's core body temperature according to a method 300 illustrated by the flowchart of FIG. 3. As set forth below, the method 300 includes calibrating the thermometer unit 100 so that the thermometer unit 100 accurately determines the core temperature data 142 in any environment in which the thermometer unit 100 and the system 101 are located.

Figure 4:
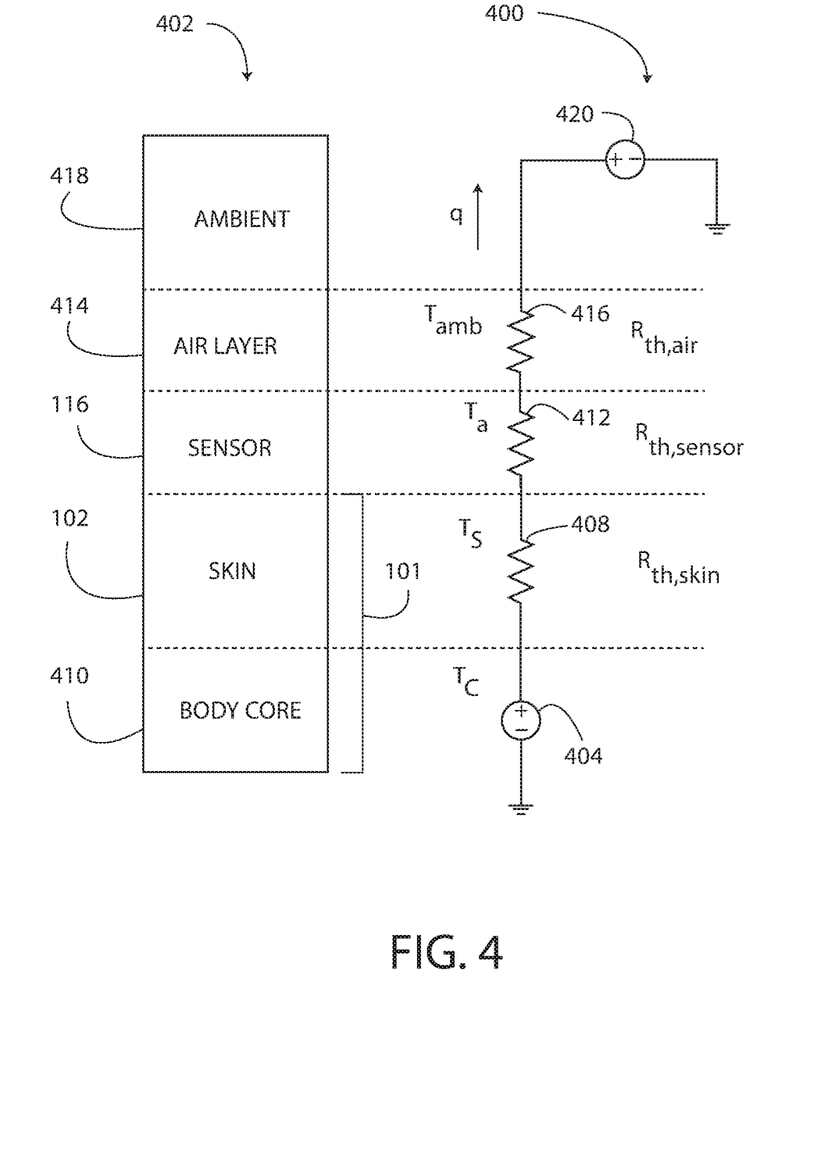
FIG. 4 is a diagram of an arrangement and a schematic of an electrical model of heat transfer through a human body.

With reference to FIG. 4, the method 300 is based on an electrical circuit model 400 of heat transfer through an arrangement 402. The arrangement 402 includes the system 101, the sensor assembly 116, an air layer 414, and an ambient area 418. The system 101 is modeled as a body core 410 and the skin 102 (all layers). The body core 410 corresponds to the portion of the system 101 internal to the skin 102. The air layer 414 corresponds to the air near the thermometer unit 100. The ambient area 418 corresponds to the temperature of the space in which the system 101 and the temperature unit 100 are located.

The electrical model 400 represents a static portion of the heat transfer through the arrangement 402; and is configured to model a steady state condition of the arrangement 402 without modeling all thermal capacities. The model 400 includes a voltage source 404 electrically connected to a series connection of a skin resistor 408, a sensor resistor 412, an air resistor 416, and another voltage source 420. The voltage source 404 models the core temperature of the body core 410. The magnitude of the voltage of the voltage source 404 corresponds to the temperature generation/output of the patient. In one embodiment, the magnitude of the voltage source 404 corresponds to the patient's core body temperature.

The skin resistor 408 exhibits an electrical resistance that corresponds to a thermal resistance of the patient's skin 102. The skin thermal resistance is a resistance of the patient's skin 102 to changes in temperature. The electrical resistance of the skin resistor 408 is based on a total thermal resistance of each layer of the patient's skin 102 including the epidermis 103a, the dermis 103b, and the hypodermis 103c.

The sensor resistor 412 exhibits an electrical resistance that corresponds to a thermal resistance of the sensor assembly 116 to changes in temperature. The sensor thermal resistance is a resistance of the sensor assembly 116 to changes in temperature. Specifically, the electrical resistance of the sensor resistor 412 corresponds to the thermal resistance of the temperature sensor 154 and the thermal resistance of the heat flux sensor 162.

The air resistor 416 exhibits an electrical resistance that corresponds to a thermal resistance of the air layer 414 adjacent to the patient's skin 102. The air thermal resistance is a resistance of the air proximate to the thermometer unit 100 to changes in temperature.

The magnitude of the voltage source 420 corresponds to the temperature generation/output of the ambient area 418 (or ambient environment) surrounding the patient. In one embodiment, the ambient area 418 includes at least the environment surrounding the sensor assembly 116, the housing 128, the air proximate to the thermometer unit 100, and/or clothing near the thermometer unit 100. The voltage sources 404, 420 oppose each other, such that voltage from the voltage source 404 opposes voltage from the voltage source 420.

As shown in the following chart, for each electrical variable of the model 400 there is a corresponding thermal variable corresponding to the patient and/or the patient's environment.

| Thermal | | | Electrical | | |
|---|---|---|---|---|---|
| Variable | Symbol | Unit | Variable | Symbol | Unit |
| Temperature | T | K | Voltage | V | V |
| Heat Transfer Rate | q | W | Current | I | A |
| Heat Flux | Q" | W/m² | Current density | J | A/m² |
| Thermal Resistance | $R_{th}$ | K/W | Resistance | R | Ω |
| Thermal Capacity | $C_{th}$ | Ws/K | Capacitance | C | As/V |

According to the chart, temperature ("T") corresponds to voltage ("V"), heat transfer rate ("q") corresponds to electrical current ("I"), heat flux ("Q'''") corresponds to electrical current density ("J"), thermal resistance ("$R_{th}$") corresponds to electrical resistance ("R"), and thermal capacity ("$C_{th}$") corresponds to electrical capacity ("C").

The electrical model 400 and the thermal equivalents are manipulated below in order to determine a thermal time constant value ("τ") of the skin 102. In an exemplary embodiment, a thermal conductivity value ("k"), a specific thermal capacity value ("$c_p$"), and a density value ("p") of the skin 102 are assumed to have constant values for all patients, since the composition of the skin 102 is substantially the same across all patients. The thermal time constant value ("τ") is based on the time required to heat or cool a material by 63.2% from an initial temperature to a different temperature. The percentage is an approximation defined as (1-$e^{-1}$), where ("e") is Euler's number, which is a constant.

Based on the above chart and model 400, Ohm's law is written using the corresponding thermal variables. To begin, using electrical variables, Ohm's law solved for electrical current can be written as equation (1).

$$I = \frac{\Delta V}{R} \quad (1)$$

Replacing the electrical variables in equation (1) with the corresponding thermal variables from the chart yields equation (2), which determines the heat transfer rate.

$$q = \frac{\Delta T}{R_{th}} \quad (2)$$

Moreover, electrical current density can be written as shown in equation (3).

$$J = \frac{\Delta V}{R \cdot \text{Area}} \quad (3)$$

Replacing the electrical variables in equation (3) with the corresponding thermal variables yields equation (4), which is an equation used to determine heat flux in a system, since in the model 400 electrical current density corresponds to the heat flux. The Area variable is a surface area and is the same in both the electrical variables and the thermal variables. Typically, the Area variable corresponds to a surface area of the area being measured for temperature. Also, the Area may be the area sensed by the heat flux sensor 162.

$$\dot{Q}'' = \frac{\Delta T}{R_{th} \cdot \text{Area}} \quad (4)$$

For each material layer (i.e. layers 103a, 103b, 103c of the skin 102, for example) a thermal resistance can be calculated with equation (5).

$$R_{th} = \frac{\Delta x}{k \cdot \text{Area}} = \frac{1}{h \cdot \text{Area}} \quad (5)$$

In equation (5), Δx corresponds to a thickness of the material layer and k corresponds to the thermal conductivity of the layer. In one embodiment, the thermal capacity of the patient/system is also calculated using a material parameter, but such a calculation is not used to determine the core body temperature of the patient. As a result, the thermal capacity is not calculated by the thermometer unit 100 in some embodiments.

The heat flux sensor 162 is configured to measure the heat flux ("Q'''") through the sensor assembly 116 at the surface of the skin 102. In one embodiment, a simplification is made that the heat flow through the skin 102 and the sensor assembly 116 is only perpendicular to the skin layer 103a (i.e. the skin 102), and that the heat flux through the skin 102 equals the heat flux through the heat flux sensor 162. Based on the above, a temperature difference (i.e. a change in temperature) across the skin 102 is modeled by equation (6).

$$\times T = T_C - T_S \quad (6)$$

In equation (6), ΔT is the change in temperature between two physical locations at the same instance in time, $T_C$ is core body temperature, and $T_S$ is the surface temperature of the skin 102. Typically, for a human system 101 the core body temperature is greater than the surface temperature of the skin 102. The core body temperature can be calculated with the following equation (7).

$$T_C = \frac{\dot{Q}''}{h_s} + T_S \quad (7)$$

In equation (7), the change in temperature ("ΔT") has been replaced with the heat flux through the sensor assembly 116 as detected by the heat flux sensor 162 (i.e. Q") divided by a heat transfer coefficient of the skin ("hs"). The heat transfer coefficient ("hs") depends on the thermal conductivity of the skin 102 (i.e. one over the thermal resistance of the skin 102) and the area through which the heat flux is measured (i.e. the variable Area). Based on the above equation, the heat transfer coefficient ("hs") may be described by equation (8).

$$h_s = \frac{1}{R_{th} \text{Area}} \quad (8)$$

The heat transfer coefficient ("hs") depends on the thickness of the skin 102 as noted by the inclusion of the thermal resistance of the skin 102 in equation (8). The hypodermis 103c (i.e. fat layer) contributes the most to the thickness of the skin 102. Moreover, the thickness of the hypodermis 103c has a large range from person to person and from region to region of a particular person. For example, the hypodermis 103c is typically thinner at the patient's wrist than at the patient's waist. Thus, in operation, the actual thickness of the hypodermis 103c depends on the selected temperature measuring spot on the patient's body, which is based on at least the gender, weight, height, and body mass index of the patient. With usage of the above-descried factors the heat transfer coefficient of the skin ("hs") can be roughly estimated. For an optimal core body temperature calculation according to the method 300, the heat transfer coefficient ("hs") is adjusted to account for environmental influences 180, as described below.

Considering again the flowchart of FIG. 3, the method 300 uses the sensor assembly 116 and the heat transfer coefficient ("hs") to determine the core temperature of the system 101, which in this example is a human body and is referred to as a patient. The method 300 begins with the thermometer unit 100 mounted on the patient or held against the patient, with the sensors 154, 162 of the sensor assembly 116 against the skin 102 of the patient. For example, the sensor assembly 116 is held in place during the core temperature sensing process to enable the heat flux sensor 162 to contact fully the skin 102 over the entire Area. When placed in contact with the patient's skin 102, the sensor assembly 116 generates the skin temperature data 146 and the heat flux data 150, which are both stored in the memory 120. As explained below, the thermometer unit 100 is configured to adjust the value of the heat transfer coefficient ("hs") to calibrate the thermometer unit 100 in response to changes in the environment in which the thermometer unit 100 and the patient are located.

At block 302, the controller 124 determines if the heat transfer coefficient ("hs") should be estimated. In one embodiment, the controller 124 determines that a first heat transfer coefficient ("hs") should be estimated when the thermometer unit 100 is configured for a different patient or when the user changes/updates data pertaining to the patient that is saved in the memory 120. In one embodiment, the first heat transfer coefficient ("hs") is estimated based on known factors, known values, and/or known constants of the system 101. For example, when the system 101 is a patient, the first heat transfer coefficient ("hs") is estimated based on an estimated thickness of the skin 102, a weight of the patient, a gender of the patient, and/or a BMI of the patient. The heat transfer coefficient ("hs") is not changed each time the thermometer unit 100 is operated. Instead, the thermometer unit 100 is used with the previously determined heat transfer coefficient ("hs") until it is determined that recalibration or adjustment should be performed.

At block 304 of the method 300, the thermometer unit 100 determines and/or recalculates the heat transfer coefficient ("hs"). To determine the heat transfer coefficient ("hs") (i.e.

a second heat transfer coefficient ("hs")), the thermometer unit 100 detects the surface temperature of the skin 102 using the temperature sensor 154, and the thermometer unit 100 detects the heat flux of the skin 102 using the heat flux sensor 162. Then, using the temperature data 146, the heat flux data 150, and the equations set forth above (saved as the program instructions 138), the thermometer unit 100 determines the heat transfer coefficient ("hs"), which is stored in the memory 120 as heat transfer coefficient data.

Next, block 308 includes using the sensor assembly 116 to monitor the core temperature of the patient. Monitoring the core temperature includes periodically or continuously measuring the surface temperature of the skin 102 with the temperature sensor 154 and measuring the heat flux with the heat flux sensor 162. Then, using the equations set forth above (saved as the program instructions 138), the controller 124 generates the core temperature data 142, which is stored in the memory 120.

According to this approach, the thermometer unit 100 is configured to determine accurately the core temperature of the patient. The core temperature data 142 may be displayed on the display 112 for viewing by a user of the thermometer unit 100 or by the patient. Additionally or alternatively, the core temperature data 142 is sent to any end device 176, such as a smartphone, using the communication unit 170 over the Internet, for example. In one embodiment, the core temperature is continuously or periodically determined and stored as the core temperature data 142 in the memory 120. The core temperature may be determined and updated every second, for example.

Next, in block 312 of FIG. 3, the controller 124 determines if an environmental influence 180 (FIGS. 5 and 6) has occurred. The environmental influence 180 is a change in the environment proximate to the thermometer unit 100 and the system 101, which results in the thermometer unit 100 having to be calibrated. Exemplary environmental influences 180, as that term is defined herein, include abrupt changes of the ambient temperature near the patient (i.e. an ambient air temperature) and proximate the temperature unit 100, as may occur when the patient moves from a first room having a first room temperature to a second room having a second room temperature that is different from the first room temperature. The temperature proximate the temperature unit 100 includes the temperature within a sphere having a radius of about one foot originating at the temperature unit 100. Other environmental influences 180 include adding or removing a covering, a layer of clothing, fabric, a blanket, or the like from the thermometer unit 100 that changes an ambient temperature in the space proximate to the thermometer unit 100. Further environmental influences 180 include increasing or decreasing humidity in the air, and the patient moving to or from a region of direct sunlight/shadow. Additional environmental influences 180 include changing or replacing the adhesive portion 105, changing the location of the thermometer unit 100 from a first region of skin 102 with little hair to a different region of skin 102 with more hair (and vice versa), operating the thermometer unit 100 on a patient that begins to sweat or that stops sweating, and changing the location of the thermometer unit 100 from a first region of skin 102 with less dirt or other impurities to a different region of skin 102 with more dirt or other impurities (and vice versa).

Any other influence that changes the temperature of the air near the skin 102 of the patient and the thermometer unit 100, but that does not change the core temperature of the patient is included as an environmental influence 180. That is, the environment influence 180 changes the temperature around the thermometer unit 100, but does not change the core temperature of the patient.

For example, if the thermometer unit 100 and the patient are covered with a blanket, then an environmental influence includes uncovering the thermometer unit 100 so that the thermometer unit 100 is no longer covered by the blanket. Uncovering the thermometer unit 100 induces a change in the air layer 414 (as modeled by the resistor 416) that causes the heat flux to change. In connection with the electrical model 400, the environmental influence 180 may change the value of the air resistor 416 and the magnitude of the voltage source 420. The environmental influence 180 does not change the value of the voltage source 404.

Figure 5:
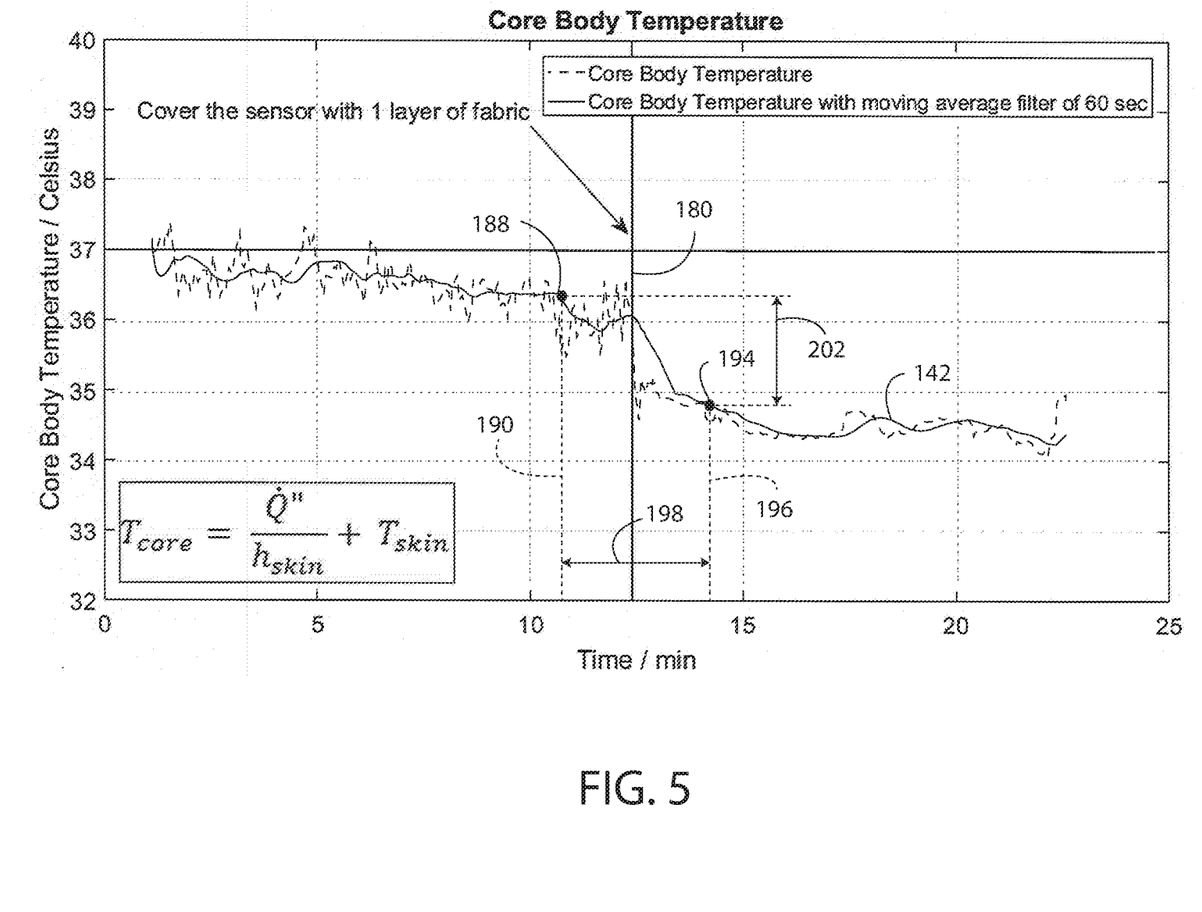
FIG. 5 is a graph of core body temperature versus time in which a heat transfer coefficient is not adjusted in response to an environmental influence.

With reference to FIG. 5, the thermometer unit 100 is configured to detect the environmental influence 180 based on a "sudden" change in the core temperature data 142. FIG. 5 illustrates a plot of the core temperature data 142 as generated by the thermometer unit 100. At about 12.5 minutes the environmental influence 180 occurs (represented by the vertical line), which causes the thermometer unit 100 to sense (incorrectly) that the core temperature of the patient has dropped very suddenly by about 2.0° C. in the course of only about four minutes. Such a sudden drop in the core temperature of patient is typically impossible when the patient is in a "room temperature" ambient environment.

An exemplary environmental 180 influence corresponding to the core temperature data 142 of FIG. 5 is the removal of a fabric layer (i.e. a blanket or shirt) from the thermometer unit 100 and the patient, which causes the air temperature around the patient and the thermometer unit 100 to decrease. In FIG. 5, no adjustment of the heat transfer coefficient ("hs") is made and, after the environmental influence 180, the core temperature data 142 is not representative of the actual core body temperature of the patient.

The environmental influence 180 changes the temperature of the ambient environment but does not change the temperature of the system (to any significant extent) because the thermal time constant of the system 101 is very much greater than the thermal time constant of the ambient environment surrounding the thermometer unit 100. In an example, the core temperature of a human typically varies about 1.0° C. over the duration of a day, and the core temperature reacts very slowly to changes in the ambient environment. The exemplary temperature change in FIG. 5 of about 2.0° C. in the course of only four minutes is far too sudden of a temperature change to have been exhibited by the patient. That is, the sudden drop in the values of core temperature data is indicative of the environmental influence 180 and is not indicative of the actual core temperature of the patient, because for any reasonable temperature in which the patient is located, the core temperature cannot react to changes in the ambient environment so quickly.

To this end, the system 101 defines a first thermal time constant and the ambient environment surrounding the patient and the thermometer unit 100 defines a second thermal time constant. The first thermal time constant of the system 101 is at least ten times greater than the second thermal time constant. As a result, changes in temperature around the thermometer unit 100 impact the sensors 154, 162 much more quickly than the changes in temperature affect the core temperature of the system 101. Because it is known that the core temperature reacts so slowly to changes in the environment, a sudden change of the core temperature data 142 is indicative of mistakes at the measurement site, noise, or a wrong calculation of the core temperature.

In a specific embodiment and with continued reference to FIG. 5, the thermometer unit 100 is configured to determine that the environmental influence 180 has occurred. To begin, the controller 124 identifies a first core temperature 188 at a first time 190 and a second core temperature 194 at a second time 196. The first time 190 is before the environmental influence 180 and the second time 196 is after the environmental influence 180. The first core temperature 188 and the second core temperature 194 are determined based on the same heat transfer coefficient ("hs") and are stored in the memory 120 as the temperature data 146. A predetermined time period 198 is defined from the first time 190 to the second time 196. The predetermined time period 198 has a duration of approximately three minutes, for example. The duration of the predetermined time period 198 is selected to be much less than the time constant of the system 101; for example, 0.5% of the time constant of the system 101.

Next, the controller 124 is configured to determine a temperature difference 202 as a difference between the first core temperature 188 and the second core temperature 194. If the temperature difference 202 is less than a predetermined temperature difference threshold, then the controller 124 determines that an environmental influence 180 has not occurred. Whereas, if the temperature difference 194 is greater than the predetermined temperature difference threshold, then the controller 124 determines than an environmental influence 180 has occurred. The magnitude of the predetermined temperature difference threshold depends on the type of system 101 monitored by the temperature unit 100. When the system 101 is a human patient, an exemplary predetermined temperature difference threshold is from about 0.5° C. to about three degrees Celsius (3° C.). In other embodiments, the predetermined temperature difference threshold is from 0.1° C. to ten degrees Celsius (10° C.). As shown in the example of FIG. 5, the temperature difference 202 is about 2° C. and the temperature threshold is 0.75° C. Thus, the controller determines that in FIG. 5 an environmental influence 180 has occurred.

As shown in block 312 of FIG. 3, if the controller 124 determines that an environmental influence 180 did not occur, then the temperature unit 100 continues to calculate the core temperature, as identified in block 308 of the method 300.

If, however, at block 312 the controller 124 determines that an environmental influence 180 did occur, then the controller 124 recalibrates the temperature unit 100 to accurately determine the core temperature. In particular, the controller 124 recalculates the heat transfer coefficient ("hs") to correspond to the present conditions of the ambient environment in which the temperature unit 100 is presently located. Moreover, in some embodiments, the controller 124 deletes the inaccurate core temperature data (such as the second core temperature data 194) that was generated after the environmental influence 180 and generates additional core temperature data based on the recalculated heat transfer coefficient ("hs") (i.e. a recalculated core temperature stored as third core temperature data in the memory 120).

Next the method 300 includes, at block 308, calculating the core temperature according to the recalculated heat transfer coefficient ("hs"). Moreover, the method 300 cycles through block 312 to continue monitoring for further environmental influences 180 that result in an additional change to the heat transfer coefficient ("hs").

The temperature unit 100 and the corresponding method 300 solve a technical problem in the art. The technical problem is that known core temperature detection apparatus generate inaccurate temperature data when an environment in which the apparatus is located undergoes a change in temperature and/or humidity. The temperature unit 100 solves this technical problem by calibrating the unit 100 after the environmental influence 180 by determining a new value of the heat transfer coefficient ("hs"). The temperature unit 100 is configured to identify sudden changes in the core temperature data 142 that are simply not possible (i.e. not indicative of an actual change in the core temperature of the system) based on the corresponding thermal time constant of the system 101 being measured.

Figure 6:
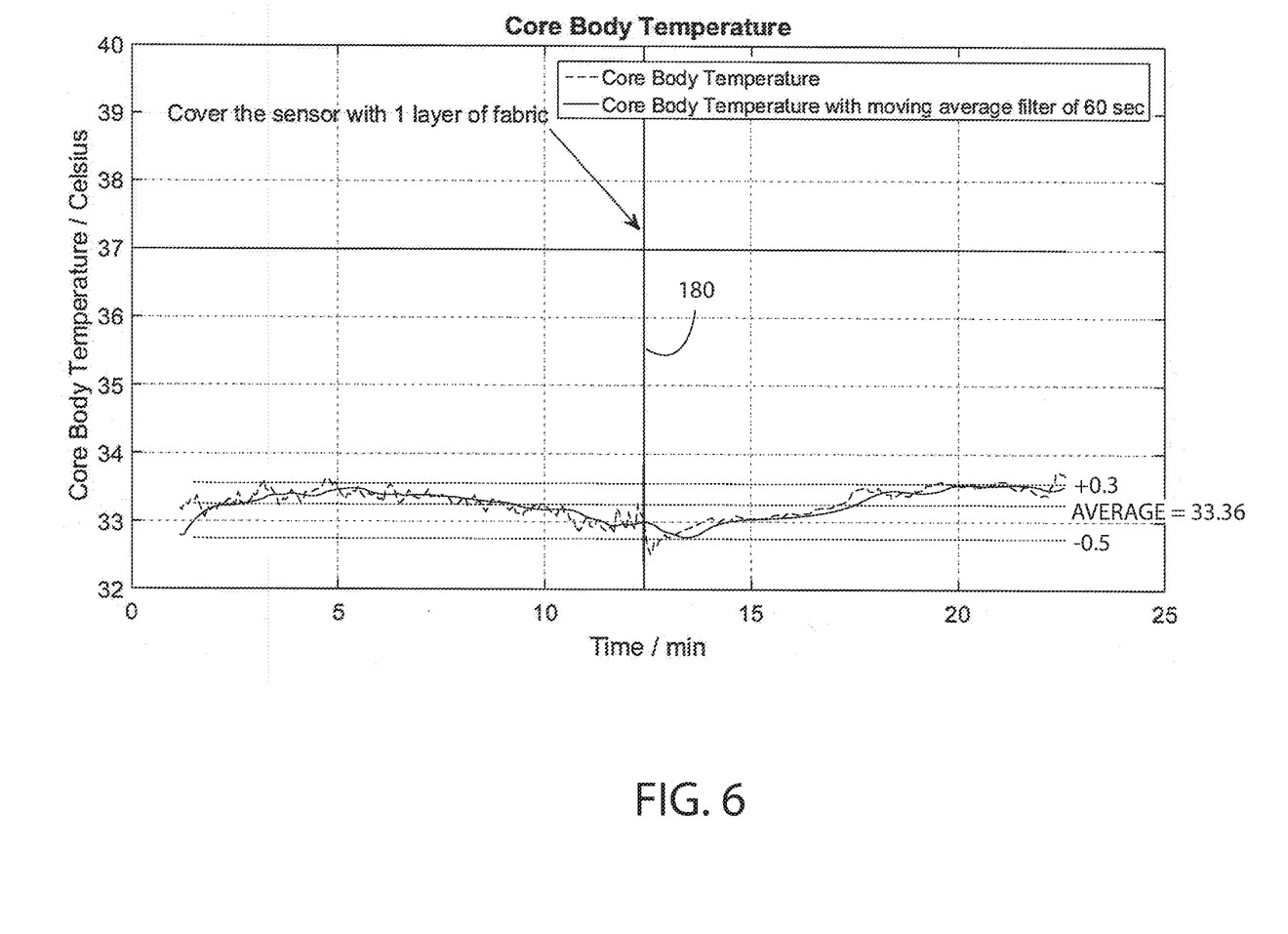
FIG. 6 is a graph of core body temperature versus time in which a heat transfer coefficient is adjusted in response to the environmental influence.

With reference to FIG. 6, an approach for determining the recalculated heat transfer coefficient ("hs") after an environmental influence 180 is illustrated. In FIG. 6, shortly after the controller 124 identifies that the environmental influence 180 occurs, the thermometer unit 100 adjusts/changes the value of the heat transfer coefficient ("hs") until the calculated core temperature returns to the same core temperature as shortly before the environmental influence. The thermometer unit 100 is configured to recognize that it is very unlikely (impossible) for the actual core body temperature of the patient to drop 1.5° C. in only a few seconds (as shown in FIG. 6 near the environmental influence 180), because the body's thermal time constant is simply too large to permit such a drastic change. Thus, the thermometer unit 100 assumes that no actual change in core body temperature has occurred in response to the environmental influence 180, and the thermometer unit 100 changes the value of the heat transfer coefficient ("hs") in the equation used to calculate the core body temperature (i.e. equation (7)). The change in the value of the heat transfer coefficient ("hs") accounts for and calibrates the thermometer unit 100 to the "new" environment established by the environmental influence 180. In FIG. 6, the thermometer unit 100 calculates again the core temperature using the updated/changed value of the heat transfer coefficient ("hs") (i.e. at block 308 of FIG. 3). Using the updated/changed value of the heat transfer coefficient ("hs") enables the thermometer unit 100 to continue to determine/calculate an accurate value for the core temperature. Specifically, after a moving average filter of sixty seconds, the calculated core temperature stays in a tolerance of +0.3° C. and −0.5° C. The offset of the core body temperature of around 4° C. has other causes like measurement inaccuracy.

Disclosed embodiments of the thermometer unit 100 include a calculation of the core body temperature of a patient, whereby the heat transfer coefficient ("hs") is adjusted, due to changes in the environment, which have an influence on the heat flow. The adjusted heat transfer coefficient ("hs") not only includes the influence of the skin 102, but also other influences on the heat flow, like other elements of the sensor setup and the layer composition. In one embodiment, to calculate the core body temperature, the thermometer unit 100 measures only the skin temperature and the heat flux with the sensor assembly 116.

Moreover, the core body temperature determination/calculation method 300 disclosed herein, can also be applied to determine the core temperature of a system 101 configured as a machine (i.e. a non-living object). For example, a machine defines a core temperature and an external temperature surrounds at least a portion of the machine. In this example, the method 300 disclosed herein is usable to determine the core temperature of the machine so long as the external temperature changes faster (e.g. 10× faster) than the core temperature.

The method 300 also enables the value of the heat transfer coefficient ("hs") to be determined from the data collected by the sensor assembly 116. Specifically, if the thermal properties of the layer composition of the skin 102 or other material are known, then the thermometer unit 100 can determine the heat transfer coefficient of the skin ("hs") (or other material) from the data collected by the sensor assembly 116. The thermal properties of the sensor assembly 116 can be determined in advance (i.e. the resistance of the sensor resistor 412 in the electrical model 400), because the thermal properties of the sensor assembly 116 do not change over time, from person to person, or in response to the environmental influences. Also, to account for the thermal influence of humidity or sweat, the thermometer unit 100 may include a humidity sensor (not shown). Another benefit of determining the heat transfer coefficient of the skin ("hs") is that the known coefficient ("hs") enables the thermometer unit 100 to estimate a thickness of the hypodermis 103c. Such information is beneficial in areas of health and fitness.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method for determining a core temperature of a system with a thermometer unit, comprising:
    sensing a surface temperature of the system using a temperature sensor and generating temperature data corresponding to the sensed surface temperature using a controller of the thermometer unit;
    sensing a heat flux of the system using a heat flux sensor and generating heat flux data corresponding to the sensed heat flux using the controller;
    calculating a first core temperature of the system based on a first sensed surface temperature of the temperature data, a first sensed heat flux of the heat flux data, and a heat transfer coefficient at a first time with the controller, the controller operably connected to the temperature sensor and the heat flux sensor;
    storing the calculated first core temperature as first core temperature data in a memory unit of the thermometer unit, the memory unit operably connected to the controller;
    calculating a second core temperature of the system based on a second sensed surface temperature of the temperature data, a second sensed heat flux of the heat flux data, and the heat transfer coefficient at a second time after the first time with the controller;
    storing the calculated second core temperature as second core temperature data in the memory unit;
    determining temperature difference data as a difference between the calculated first and second core temperature data with the controller;
    when the temperature difference data is greater than a predetermined temperature difference threshold (i) recalculating the heat transfer coefficient with the controller, (ii) deleting the second core temperature data from the memory, and (iii) calculating a third core temperature of the system based on the recalculated heat transfer coefficient; and
    storing the recalculated core temperature as third core temperature data in the memory.

2. The method as claimed in claim 1, wherein:
    the system and the thermometer unit are subjected to an environmental influence,
    the environmental influence results in the temperature difference data being greater than the predetermined temperature difference threshold, and
    the environmental influence does not change the core temperature.

3. The method as claimed in claim 2, wherein:
    the system is a human body,
    the thermometer unit is mounted on the human body, and
    the environmental influence changes an ambient temperature proximate to the thermometer unit.

4. The method as claimed in claim 3, wherein:
    the environmental influence includes the human body moving from a first room at a first room temperature to a second room at a second room temperature, and
    the first room temperature is different than the second room temperature.

5. The method as claimed in claim 2, wherein:
    the environmental influence includes applying or removing a covering from the thermometer unit, and
    the covering is configured as a blanket or a layer of clothing.

6. The method as claimed in claim 1, wherein recalculating the heat transfer coefficient with the controller includes:
    adjusting a value of the heat transfer coefficient so that the third core temperature is the same as the first core temperature.

7. The method as claimed in claim 1, wherein:
    the system defines a first thermal time constant,
    an ambient environment surrounding the system and the thermometer unit defines a second thermal time constant, and
    the first thermal time constant is at least ten times greater than the second thermal time constant.

8. A thermometer unit for determining a core temperature of a system, comprising:
    a temperature sensor configured to sense a surface temperature of the system and to generate temperature data corresponding to the sensed surface temperature;
    a heat flux sensor configured to sense a heat flux of the system and to generate heat flux data corresponding to the sensed heat flux;
    a memory configured to store the temperature data and the heat flux data; and
    a controller operably connected to the temperature sensor, the heat flux sensor, and the memory and configured to determine core temperature data corresponding to a core temperature of the system, the controller configured to calibrate the thermometer unit in response to an environmental influence by:
        calculating, at a first time, a first core temperature data based on a first sensed surface temperature, a first sensed heat flux, and a heat transfer coefficient;
        calculating, at a second time, a second core temperature data based on a second sensed surface temperature, a second sensed heat flux, and the heat transfer coefficient; and
        calibrating the thermometer unit when a difference between the first core temperature data and the second core temperature data exceeds a predetermined threshold value by calculating another heat transfer coefficient.

9. The thermometer unit as claimed in claim 8, wherein:
    the thermometer unit is configured to contact skin,
    an environmental influence changes an ambient temperature proximate to the thermometer unit, and
    the environmental influence does not change the core temperature.

10. The thermometer unit as claimed in claim 8, wherein the environmental influence includes placing a layer over the thermometer unit or removing the layer from the thermometer unit.

11. The thermometer unit as claimed in claim 8, wherein:
the system defines a first thermal time constant,
an ambient environment proximate to the system and the thermometer unit defines a second thermal time constant, and
the first thermal time constant is at least ten times greater than the second thermal time constant.

12. The thermometer unit as claimed in claim 8, further comprising:
an energy harvester with a power management circuit configured to supply the thermometer unit with electrical energy.

13. A method for calibrating a thermometer unit for measuring a core temperature of a system, comprising:
determining a first heat transfer coefficient of the system;
sensing a surface temperature of the system using a temperature sensor and generating temperature data corresponding to the sensed surface temperature using a controller of the thermometer unit;
sensing a heat flux of the system using a heat flux sensor and generating heat flux data corresponding to the sensed heat flux using the controller;
calculating core temperature data corresponding to the core temperature of the system based on the first heat transfer coefficient, the temperature data, and the heat flux data using the controller;
identifying a change in the core temperature data that exceeds a predetermined threshold using the controller; and
calibrating the thermometer unit by (i) determining a second heat transfer coefficient in response to the identified change in the core temperature data, and (ii) calculating the core temperature data based on the second heat transfer coefficient, the temperature data, and the heat flux data using the controller.

14. The method as claimed in claim 13, further comprising:
estimating the first heat transfer coefficient based on at least one known constant of the system; and
determining the second heat transfer coefficient based on a measured surface temperature of the system.

15. The method as claimed in claim 13, further comprising:
exposing the system and the thermometer unit to an environmental influence that changes a temperature of an ambient environment proximate the thermometer unit but that does not change the core temperature; and
detecting the exposure to the environmental influence by identifying the change in the core temperature data.

* * * * *